United States Patent [19]

Kreuter et al.

[11] 4,269,821

[45] May 26, 1981

[54] BIOLOGICAL MATERIALS

[75] Inventors: Jörg Kreuter, 25 Münstergasse, CH-8001 Zurich; Peter P. Speiser, 26 Wassbergstrasse, CH-8127 Forch, both of Switzerland

[73] Assignees: Jörg Kreuter; Peter Paul Speiser, both of Basel, Switzerland

[21] Appl. No.: 146,018

[22] Filed: May 2, 1980

Related U.S. Application Data

[60] Division of Ser. No. 931,680, Aug. 7, 1978, Pat. No. 4,225,581, which is a continuation of Ser. No. 862,213, Dec. 19, 1977, abandoned, which is a continuation of Ser. No. 666,611, Mar. 15, 1976, abandoned.

[30] Foreign Application Priority Data

Mar. 20, 1975 [CH] Switzerland .......................... 3573/75
May 13, 1975 [CH] Switzerland .......................... 6125/75

[51] Int. Cl.$^3$ ...................... A61K 37/26; A61K 9/14; A61K 9/52; A61K 9/58
[52] U.S. Cl. ....................................... 424/19; 424/22; 424/32; 424/33; 424/81; 424/177
[58] Field of Search .............. 427/1; 252/316; 424/16, 424/32, 33, 81, 88, 89, 92

[56] References Cited

U.S. PATENT DOCUMENTS 4,021,364  5/1977  Speiser et al. ........................ 252/316
4,107,288  8/1978  Oppenheim et al. ................... 424/22
4,225,581  9/1980  Kreuter et al. ......................... 424/88

OTHER PUBLICATIONS

Marty et al., Pharm. Acta. Helv. 53(1):17–23 (1978) Nanoparticles–A New Colloidal Drug Delivery System.
Marty et al., Australian J. Pharm. Sci. 6(3):65–75, Sep. 1977, Colloidal Systems for Drug Delivery.
Kreuter, Pharm. Acta. Helv. 53(2):33–39 (1978) Nanoparticles and Nanocapsules–New Dosage Forms in the Nanometer Size Range.
Birrenbach, G., Diss. Eth Zurich (1973) p. 62ff, Uber Mizellpolymerisate Mogliche ein Schlussver Bindungen (Nanokapseln) und Deren Gignung Als Adjuvantion.

Primary Examiner—Shep K. Rose
Attorney, Agent, or Firm—Gerald D. Sharkin; Robert S. Honor; Walter F. Jewell

[57] ABSTRACT

There are described processes for the preparation of submicroscopic particles of physiologically acceptable polymer associated with a biologically active material, by polymerizing a monomer in the presence of the biologically active material or by adsorbing the biologically active material upon preformed submicroscopic polymer particles. Where the biologically active material is an antigen, the particles are useful as constituents of injectable vaccines having an adjuvant effect.

2 Claims, No Drawings

BIOLOGICAL MATERIALS

This is a division of application Ser. No. 931,680, filed Aug. 7, 1978, now U.S. Pat. No. 4,225,581, which in turn is a continuation, of application Ser. No. 862,213, filed Dec. 19, 1977, now abandoned, which in turn is a continuation, of application Ser. No. 666,611, filed Mar. 15, 1976, now abandoned.

This invention relates to methods for increasing the effectiveness of biologically active materials, for example injectable vaccines, and to the products so obtained.

The invention provides a process for the preparation of submicroscopic particles of a physiologically acceptable polymeric material which are capable of forming a suspension or colloidal solution in a hydrophilic or hydrophobic liquid medium and which are associated with a biologically active material, characterised by the polymerisation of a solution or suspension of a polymerisable material in the presence of the biologically active material, the amount of any stabilising agent present being not greater than 3% by weight of the reaction medium, or by the adsorption of biologically active material upon submicroscopic polymer particles formed by polymerisation of a polymerisable material in the absence of the biologically active material.

The process according to the invention is carried out
(a) by mixing a suspension, emulsion, solution or colloidal solution in a liquid medium of the biologically active material in the free state or adsorbed on a carrier, a polymerisable material soluble in the liquid medium and from 0–3% by weight of a stabilising agent, and causing the polymerisation of the polymerisable material, or
(b) by suspending the submicroscopic polymer particles in a liquid medium containing the biologically active material. Preferably the particles are obtained by dissolving, emulsifying or suspending a monomer in a liquid medium and carrying out polymerisation by known methods so as to obtain polymer particles of submicroscopic dimensions. The product of process (a) is a particle comprising biologically active material wholly or partly coated by an outer layer of polymeric material; that of process (b) is a particle consisting of a solid polymer core on which is adsorbed an outer layer of biologically active material.

In the process of the invention, the term polymerisation is used broadly to include addition polymerisation of a monomer or two or more comonomers, condensation polymerisation of one or more monomers or prepolymers and coacervation, in which a soluble polymeric material is converted to an insoluble form. Suitable polymerisable materials for process (a) include single monomers such as styrene, vinylpyrrolidone, acrylic monomers e.g. methyl acrylate, butyl acrylate and acrylamide and methacrylic acid derivatives e.g. methyl methacrylate, butyl methacrylate and methacrylamide and mixtures of these, for example methyl methacrylate/acrylamide. Suitable soluble prepolymers include urea-formaldehyde, phenoplast or aminoplast prepolymers, which may be further polymerised by polycondensation. Suitable materials for coacervation include gelatine and casein.

The polymerisable material must be soluble to some extent in the liquid medium, but this solubility may only be small. The liquid medium is preferably water, in which, for example, methyl methacrylate is soluble to the extent of 15 g/l at room temperature, or an aqueous solution of a physiological buffer solution, for example phosphate buffer, or physiological saline.

The polymerisation is preferably carried out in the absence of any stabilising agent. A stabilising agent, preferably a surface active agent for example sodium sulphosuccinic acid di-(2-ethylhexyl)ester (Aerosol OT) may however be used to emulsify the biologically active material or the polymerisable material. The amount of stabilising agent used, however, is not greater than 3% by weight of the reaction mixture, preferably not greater than 1% and more preferably not greater than the critical micelle concentration, which is that concentration of stabilising agent required to stabilise micelles of the discontinuous phase in the continuous phase. For methyl methacrylate in water, this figure is approximately 0.1% by weight of the water.

The preferred polymerisable material is methyl methacrylate, either alone or mixed with acrylamide. Styrene and other acrylic monomers may also be used, but in the case of acrylic and methacrylic acids, the activity of the free carboxylic acid groups may be harmful to the biologically active material used.

Biologically active materials suitable for use in the process of the invention include antigens, proteins, viruses, virus subunits, bacteria, bacteria subunits, cells and cell subunits. Preferred materials are those suitable for parenteral administration to induce immune response to infectious disease. Most preferred materials are influenza vaccines, particularly those containing influenza virus subunits.

The term "biologically active materials" also includes molecules of chemical compounds having pharmacological properties, particularly those having high molecular weight. Examples of these include peptides, e.g. insulin, and steroids particularly steroid hormones.

When the product of the polymerisation reaction is intended for parenteral administration, it is desirable that the method used should be one which gives as little by-products as possible and which gives a very pure and well-defined product, for example polymerisation initiated by $\gamma$-radiation, UV or visible light, if necessary in the presence of a suitable activator or catalyst. Preferably the polymerisation is carried out under an inert atmosphere, for example of nitrogen. If the reaction system tends to separate out on standing, vigorous stirring may be advantageous.

It is important, however, that neither the radiation nor the catalyst, if any, which is used should be such as to damage or deactivate the biologically active material. Such materials may consist of macromolecules which are easily destroyed by heat, extremes of pH, oxidation or certain types of radiation. Suitable methods of inducing addition polymerisation include:

(i) by gamma-radiation, for example from a $^{60}$Co source, in the absence of a catalyst. Normally a dose of approx. 0.5 Mrad is sufficient for quantities up to 1 g of monomer;

(ii) where the biologically active material is not sensitive to oxidation, a water-soluble free radical initiator such as a persulphate may also be used;

(iii) by irradiation with visible light, for example from a 300 watt fluorescent lamp, using riboflavin (0.01%) as sensitizer and potassium persulphate as catalyst (iv) where the biologically active material is not deactivated by UV light, this may also be used to induce polymerisation. Proteins have an accelerating effect upon the polymerisation time.

Only small quantities of the preferred polymerisable materials are required for coating of the particles of biologically active material. Thus, if the active material is a vaccine in aqueous suspension at the concentration normally used for parenteral administration, for example an influenza vaccine having a haemagglutination titre of $2^{12}$–$2^{15}$, the polymerisation of 2% (by weight of the reaction medium) of methyl methacrylate will normally cause substantially complete coating of the biologically active material. Preferably, a partial coating is obtained, for example by complete polymerisation of 0.25–1% of polymerisable material by weight of the reaction medium. Where a partial coating is referred to, it is to be understood that there will normally be a statistical distribution of the degree of coating, so that some particles may be uncoated and others completely coated.

During the polymerisation process according to the invention, the polymerisable material first becomes oriented against the solid or solvated boundary surface of the particles of active material, according to physicochemical properties such as polarity, dielectric constant, partition coefficient, etc.; builds up a coating layer, and becomes hardened by polymerisation. In addition, during the hardening process, the growing oligomers of the polymerisable material may become arranged upon the active material. There may also be an adsorption of active material upon larger polymer units, which in the course of further polymerisation can be built up into the developing particles. In this way there may result a partial enclosure or an adsorptive binding of active material.

If the molecules of active material are too small or too polar in nature, they may first be adsorbed upon a suitable carrier material, and then may be coated together with the carrier by the process of the invention. Suitable carrier materials include submicroscopic particles of aluminium hydroxide, bolus, hydrated silica (e.g. "Aerosil"), and physiologically acceptable polymeric materials. Preferably, the carrier material is the same polymeric material as that to be used in the coating layer.

The reaction product, consisting of submicroscopic particles, that is, particles of diameter less than 500 nm, preferably 50–300 nm, may be isolated from the reaction mixture by conventional methods, and if necessary purified. Alternatively, particularly if the preferred method of polymerisation is used, namely by γ-radiation in the absence of catalyst, it may be possible to use the reaction mixture for injection without further treatment.

In all cases, however, it is important to test the end product for traces of residual monomer, on account of the toxic properties of many monomers, including methyl methacrylate. For this purpose the method of F. E. Critchfield, G. L. Funk and J. B. Johnson: Anal.-chem. 28, 76 (1955) may be used.

If excessive quantities of monomer are present, a further purification step is necessary. The monomer can be washed from the particles with a suitable solvent in which the monomer, but not the polymer, is soluble. The product is then concentrated for example by centrifugation, filtration or dialysis and made up to a suitable concentration for use. Alternatively volatile monomers such as methyl methacrylate or styrene may be removed by evaporation in vacuo or freeze drying.

In process (b) the liquid medium may be hydrophilic or hydrophobic, but preferably is water or an aqueous solution of a physiological buffer solution for example phosphate buffer, or physiological saline. Suitable monomers are those described under process (a), particularly methyl methacrylate alone or together with acrylamide.

The polymerisation may be carried out by methods known for the formation of submicroscopic polymer particles, suitably by the methods (i)–(iv) listed under process (a). Although, since the polymerisation is not carried out in the presence of the biologically active material, UV radiation and oxidizing catalysts such as persulphates may be used freely, and other methods such as heating in an autoclave may be used, it is just as important to obtain a pure product and to eliminate residual monomer, as described above.

The resulting polymer particles, which are of submicroscopic dimensions, that is, less than 500 nm diameter, preferably 50–300 nm, are then contacted with the biologically active material in a liquid medium. The particles are preferably isolated or concentrated, for example by centrifugation or freeze drying, and resuspended in an aqueous medium before being added to an aqueous solution, emulsion or suspension of the biologically active material, whereby the active material becomes adsorbed upon the surface of the polymer particles. Isolation by freeze drying is particularly preferred since this process removes residual monomer and also appears to increase the adsorptive power of the particles.

Alternatively, the solution or suspension of the biologically active material may be added directly to the reaction medium in which polymerisation was carried out, omitting the step of isolating the polymer particles. This has the disadvantage, however, that a higher concentration of biologically active material is required.

Furthermore, suitable submicroscopic polymeric particles may be, or may become commercially available, in which case such ready made particles may simply be suspended in a liquid medium containing the biologically active material.

According to a further aspect of the invention, there is provided submicroscopic particles of a physiologically acceptable polymeric material on which is adsorbed a biologically active material. The invention also provides submicroscopic particles comprising a physiologically acceptable polymeric material in association with a biologically active material and prepared by process (a) above. The invention further provides submicroscopic particles comprising a biologically active material, in free state or adsorbed on a carrier, which are partially but not completely coated with a physiologically acceptable solid polymeric material.

Particles according to the invention are useful for parental administration as vaccines, particularly influenza vaccines, when the biologically active material is suitably chosen, for example when it consists of whole influenza virions or influenza virus subunits. They show an adjuvant activity, that is, they increase and/or prolong the immunological effect as compared with vaccines not containing polymeric material, as indicated by (a) increasing the antibody titre in the haemagglutination inhibition test in mice. A group of 20 female NMRI mice, weighing 20 g, are each given 62.5 CCA of influenza vaccine (A2/Hongkong X-31) intraperitoneally, the antigen being associated with polymeric material according to the present invention. Blood is taken before vaccination and after 20 days. Sera are inactivated by periodate treatment and heating at 56° for 30 min before titration. The antibody determination is performed with the HI-test using the microtiter method of O'Brien, T. C., S. Rastogi and N. M. Tauraso, Appl. Microbiol 21 311–315 (1971) in 'V' plates in the automatic pipetting machine (Autotiter III, Canalio) with 0.5% chicken erythrocytes. Antibody levels are compared with control groups receiving aqueous vaccine (i) without adjuvant and (ii) with conventional Al(OH)$_3$ adjuvant, and (b) increasing the antibody titre in the H-I test in guinea pigs. A group of 25 guinea pigs are each given 400 I.U. influenza virions (B/Hongkong 8/73) subcutaneously, the antigen being associated with polymeric material according to the present invention. Blood is taken before immunisation and after 4 and 8 weeks, the animals receiving a booster injection of 800 I.U. of the same virions without polymer after 4 weeks. The serum is inactivated with RDE (receptor destroying enzyme) and by heating at 56° before titration, which is carried out as described under (a) above. The results are compared with those of control groups as before.

In addition, particles according to the invention in which the biologically active material is a compound having pharmacological properties are useful for parenteral or oral administration in order to provide a slow release of the compound in the body, thereby prolonging the effect of the compound.

The following examples illustrate the invention:

EXAMPLES 1–7

Process (a)

EXAMPLE 1

To 50 ml aqueous influenza virus suspension having a haemagglutination titre of $2^{12}$ is added 0.4 ml methyl methacrylate and the mixture shaken, then left to stand at 4° C. for 1–3 days. The solution is then deoxygenated by bubbling a slow stream of nitrogen through it for 5 minutes, then tightly sealed and irradiated by a $^{60}$Co source at room temperature to a total dose of 0.46 Mrad. The disappearance of free monomer is checked by analyses for $\alpha,\beta$ unsaturated compounds by acidimetric colour titration using morpholine. The resulting particles may be used as vaccine without further treatment.

EXAMPLES 2, 3

Example 1 is repeated using the following monomers:
(2) 0.25 ml methyl methacrylate + 250 mg acrylamide
(3) 0.2 ml styrene.

EXAMPLE 4

Polymerisation with visible light

A solution containing polymerisable material and biologically active material as described in Examples 1–3 is placed in a double walled water-cooled cylindrical reaction vessel of Pyrex glass (light path 6 cm). To it is added with stirring 0.2 mg riboflavin-5-sodium phosphate and 0.2 mg potassium persulphate. The solution is then irradiated by an external 300 watt light bulb at a distance of 15 cm, with continual stirring, under a nitrogen stream and at a temperature of 35°±5° C. until the monomer has completely reacted (5–10 hr.)

EXAMPLE 5

Polymerisation with UV light

The reaction is carried out as described in Example 4, a UV quartz lamp (600 w.) placed internally in the inner space of the reaction vessel. The monomer is completely reacted within 1–5 hr.

EXAMPLE 6

The example illustrates the adsorption of the biologically active material on a carrier, which may be the same material as used for coating.

To 50 ml of physiological saline is added 0.8 ml methyl methacrylate, which is polymerised as described in Example 1 in the absence of biologically active material. To the resulting suspension of polymer particles is added 50 000 units of an insulin hydrochloride solution (pH 3), and the pH of the solution adjusted to pH 5.6 by addition of NaOH with stirring. The insulin is thereby absorbed upon the polymer particles. A further 0.3 ml methyl methacrylate and 200 mg acrylamide is added and polymerisation carried out again as in Example 4, using visible light.

EXAMPLE 7

Particles of polymethylmethacrylate are prepared as described in the first part of Example 6. To these are added 100 mg 13-ethyl-17-ethynyl-17$\beta$-hydroxy-4-gonen-3-one dissolved in 10 ml propylene glycol, and the mixture shaken for 15 minutes. After addition of 0.2 ml styrene, polymerisation is carried out as in Example 1.

EXAMPLES 8–13

Process (b)

EXAMPLE 8

Methyl methacrylate (1 ml) is added to 100 ml of an aqueous phosphate buffered saline solution containing 760 mg Na$_2$HPO$_4$.2H$_2$O, 145 mg KH$_2$PO$_4$ and 480 mg NaCl. The mixture is shaken and a stream of nitrogen passed through it for 5 minutes, then it is sealed in a reaction vessel and irradiated from a $^{60}$Co source with 0.46 Mrad. After polymerisation the polymer particles are concentrated by centrifugation and the supernatant discarded. The particles are washed twice with 100 ml of phosphate buffer and then shaken with 100 ml of fluid influenza vaccine having a haemagglutination titre of $2^{12}$. After testing for absence of residual monomer, the vaccine is ready for parenteral administration.

EXAMPLE 9

Methyl methacrylate (0.4 ml) is added to 50 ml physiological saline. After deoxygenating with a stream of nitrogen, the monomer is polymerised in an autoclave at 80° C. for 2 hours. The product is worked up as described in Example 8.

EXAMPLE 10

Methyl methacrylate (0.4 ml) is added to 50 ml physiological saline, together with 0.1 g potassium persulphate, and the mixture is deoxygenated with nitrogen and heated at 80° C., 1 atom pressure for 2 hours. The product is worked up as described in Example 8.

EXAMPLE 11

Example 9 is repeated, but instead of autoclave polymerisation, a five-hour to a UV lamp is used to prepare the polymer.

EXAMPLES 12–14

Example 8 is repeated, using in place of methyl methacrylate

(12) A mixture of 0.35 ml methyl methacrylate and 250 mg acrylamide.
(13) 0.2 ml styrene
(14) A mixture of 200 mg styrene and 500 mg methacrylamide.

EXAMPLE 15

To 50 ml physiological saline is added 0.8 ml methyl methacrylate, which is polymerised by γ-radiation as described in Example 8. To the resulting suspension of polymer particles is added 50 000 units of an insulin hydrochloride solution (pH 3), and the pH of the solution adjusted to pH 5-6 by addition of NaOH with stirring. The polymer particles with adsorbed insulin are isolated by centrifugation and drying.

What is claimed is:

1. Submicroscopic particles of a polymerized styrene or acrylic monomer on which is absorbed insulin, in suspension or colloidal solution in a sterile aqueous medium, wherein the submicroscopic particles have a particle size of from 50 to 500 nm diameters, whereby the submicroscopic particles are formed by suspending the polymeric particles in a liquid medium containing the insulin.

2. A method of injecting insulin particles according to claim 1.

* * * * *